Figure 1:
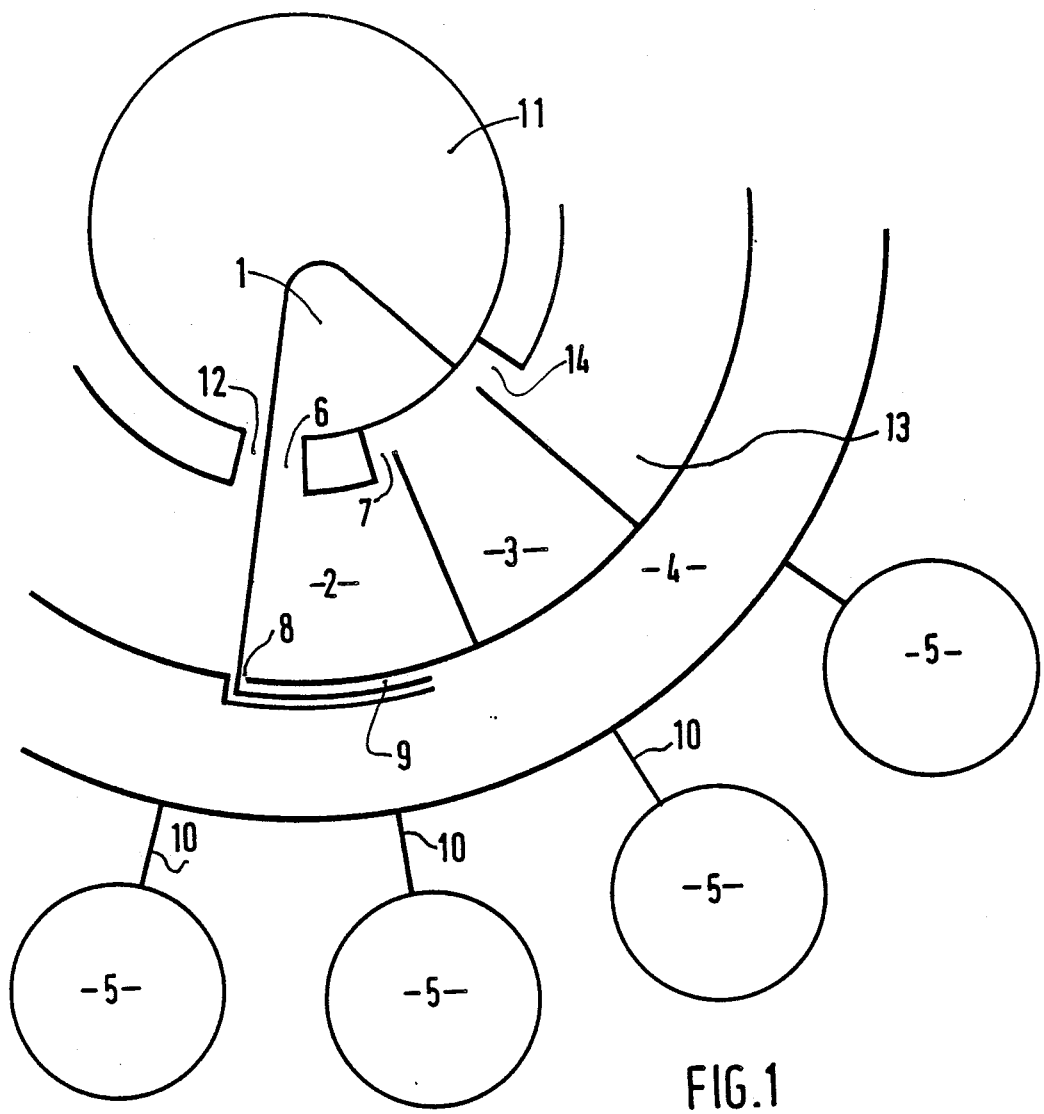

United States Patent [19]

Cornut

[11] Patent Number: 4,894,204
[45] Date of Patent: Jan. 16, 1990

[54] ROTOR WITH DYNAMIC PIPETING FOR A CENTRIFUGE ANALYSIS DEVICE

[75] Inventor: Bruno Cornut, Pau, France

[73] Assignee: Inovelf, Courbevoie, France

[21] Appl. No.: 282,855

[22] Filed: Dec. 9, 1988

Related U.S. Application Data

[63] Continuation of Ser. No. 149,530, Jan. 28, 1988, abandoned, which is a continuation of Ser. No. 810,601, Dec. 19, 1985, abandoned.

[30] Foreign Application Priority Data

Dec. 21, 1984 [FR] France .................. 84 19617

[51] Int. Cl.⁴ .......................................... G01N 21/07
[52] U.S. Cl. .................................. 422/72; 356/426; 422/102
[58] Field of Search .......... 422/72, 100; 356/426, 356/427; 436/45

[56] References Cited

U.S. PATENT DOCUMENTS 3,829,223 8/1974 Hamel .................................. 422/72
4,469,793 9/1984 Guigan ................................ 436/45

FOREIGN PATENT DOCUMENTS 62907 4/1982 European Pat. Off. .
73512 8/1982 European Pat. Off. .
39825 4/1985 European Pat. Off. .
2529245 1/1977 Fed. Rep. of Germany .

Primary Examiner—Michael S. Marcus
Attorney, Agent, or Firm—Bacon & Thomas

[57] ABSTRACT

A rotor, which has a center and a periphery, of a centrifuge analysis device. The rotor comprises, from the center of the periphery: central receptacles for liquids to be diluted before analysis; calibration vessels and overflow vessels disposed circumferentially adjacent to each other in respect to a circle concentric with the rotor; a mixing vessel communicating with each calibration vessel; and a plurality of measuring cells, each connected to the mixing vessel through a duct. Each calibration vessel is further provided with: a feed orifice through which it comunicates with one of the central receptacles; an exit orifice located in the wall of said calibration vessel opposite the feed orifice and permanently open; and an overflow orifice located at a position between said feed and exit orifices and through which the calibration vessel is connected to one of the overflow vessels. The exit orifice of each calibration vessel has a cross-sectional area much smaller as compared to that of the feed and overflow orifices, such that during the time taken to fill the calibration vessel, practically no fluid escapes from the exit orifice.

8 Claims, 4 Drawing Sheets

ROTOR WITH DYNAMIC PIPETING FOR A CENTRIFUGE ANALYSIS DEVICE

This application is a continuation of application Ser. No. 149,530, filed Jan. 28, 1988, which is a continuation of application Ser. No. 810,601, filed Dec. 19, 1985, each abandoned.

DESCRIPTIVE SUMMARY

The invention relates to a rotor for a centrifuge analysis device comprising, from the center towards the periphery: (1) central receptacles for the liquids to be diluted before analysis, (2) calibration vessels and overflow vessels, (3) a mixing vessel and (4) measuring cells.

This device is characterized in that the calibration vessels and overflow vessels are positioned circumferentially adjacent to each other in respect to a circle concentric with the rotor, the calibration and overflow vessels thereby being spaced at substantially the same distance from the center of the rotor, and wherein the calibration vessels comprise, in addition to their feed orifice and their overflow orifice, an orifice in the wall of the calibration vessel opposite the feed orifice, this orifice being permanently open and having an area which is much smaller than that of the feed and overflow orifices so that during the time taken to fill the calibration vessel practically no fluid escapes from said exit orifice. Application to rapid medical analyses.

The invention relates to a rotor for a centrifuge analysis device comprising, from the center to the periphery: (1) central receptacles for liquids to be diluted before analysis, (2) calibration vessels and overflow vessels, (3) a mixing vessel and (4) measuring cells.

Such rotors are known in the art, especially in European patent application No. 0062907. This device allows the calibration (i.e. measurement) of a liquid sample, but the arrangement of the calibration vessel and the orientation of its overflow orifice impose a flow direction on the liquid exiting from this vessel which is not favorable to the precision of the measurement and, further, forces stopping of the rotor and its rotation in the opposite direction when it is desired to pass the liquid to be analysed from the calibration vessel to the measuring cells.

The present invention provides a rotor which makes it possible to overcome these drawbacks while offering additional analytical capabilities.

To this end, the invention relates to a rotor for a centrifugal analysis device comprising, from its center to its periphery, (1) central receptacles for the liquid to be diluted before analysis, (2) calibration vessels and overflow vessels, (3) a mixing vessel and (4) measuring cells, characterized in that the calibration vessels and overflow vessels are positioned circumferentially adjacent to each other in respect to a circle concentric with the rotor, the calibration and overflow vessels thereby being spaced at substantially the same distance from the center of the rotor, and wherein the calibration vessels comprise, in addition to their feed orifice and their overflow orifice, an orifice in the wall of the vessel opposite from the feed orifice, said orifice being permanently open and having a cross sectional area which is much smaller than that of the feed and overflow orifices. This arrangement makes possible a rapid filling of the calibration vessel and an immediate removal of its overflow. Liquid begins to escape from the calibration chamber from the start of its being filled. This allows the measurement to be precise since the ratio of the filling time to the flow time from the exit orifice can be as small as desired, since it is a function of the areas of the orifices. It is also noted that movement of the liquid from the calibration vessel to the mixing vessel occurs continuously and totally, without the necessity to reverse the direction of rotation of the rotor.

According to a characteristic of the invention, the exit orifice from the calibration vessel is a capillary oriented tangentially to the wall of the calibration vessel opposite the entrance orifice. This makes it possible to increase the braking effect due to the small cross section fo the exit orifice.

It is advantageous that the mixing vessel be subdivided into several sectors each associated to two or more calibration vessels and that the exit orifices from these calibration vessels be adjacent or even flow through a common capillary into the mixing vessel. Each sector can then be used for a different analysis, one of the calibration vessels receiving for example liquid to be analysed, and the other calibration vessel or vessels receiving a reagent and/or the dilution liquid.

According to another characteristic of the invention, the exit orifice from a calibration vessel leads to a siphon whose elbow is at substantially the same distance from the center of the rotor as the overflow orifice of the calibration vessel. With this arrangement, it is sufficient to stop the rotor at the end of the filling of the calibration vessel and to allow the capillary forces to operate in the siphon so that it automatically is started without exercising additional pressure on the liquid. It is found that the small mass of liquid entrained by these capillary forces which overflows slightly from the elbow of the siphon is sufficient, when the rotor is started up again, to initiate the operation of the siphon and to draw out the liquid in the calibration vessel until it is completely empty.

According to another characteristic of the invention, the exit orifice of a calibration vessel ends at a siphon whose elbow is at a distance from the center of the rotor which is larger by a few millimeters than the distance from the overflow orifice to the center of the rotor. In contrast to the previous arrangement, the present one makes it possible to initiate the siphon action as soon as the level of the elbow is slightly exceeded, without interrupting the rotation of the rotor.

It should be noted that the presence of a siphon increases the precision of the calibration (i.e. volume measurement) since it completely eliminates or significantly decreases the necessity to take into account the flow through the exit orifice.

According to another characteristic of the invention, the calibration vessel comprises an additional volume to collect a centrifuged precipitate located beyond its exit orifice. With this arrangement, the calibration vessel empties only to the "level" of its exit orifice and the precipitate, constituted for example of red cells extracted from complete blood, is completely retained in the additional volume.

Figure 2:
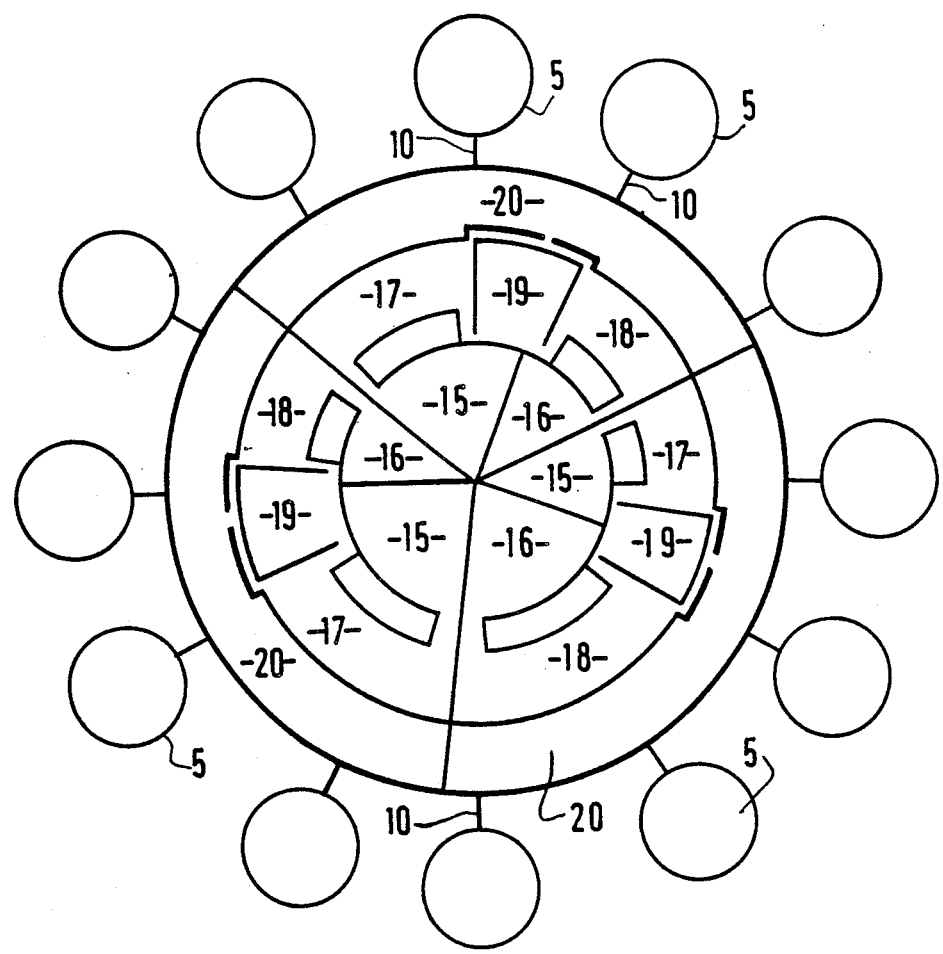
Figure 3:
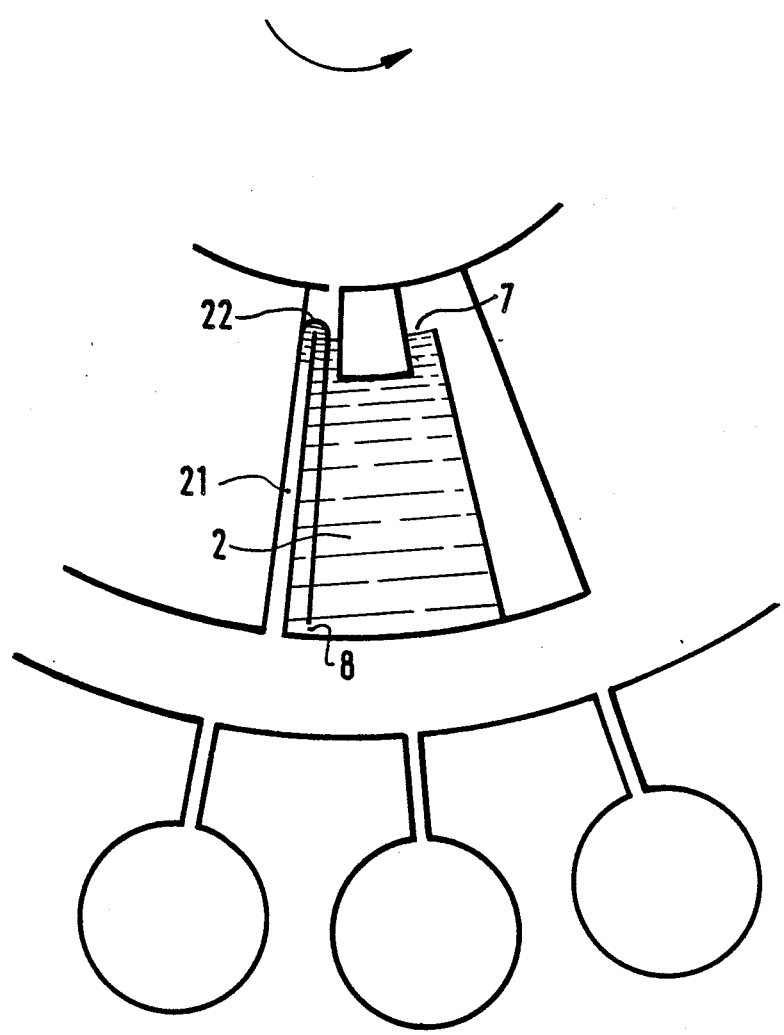
Figure 4:
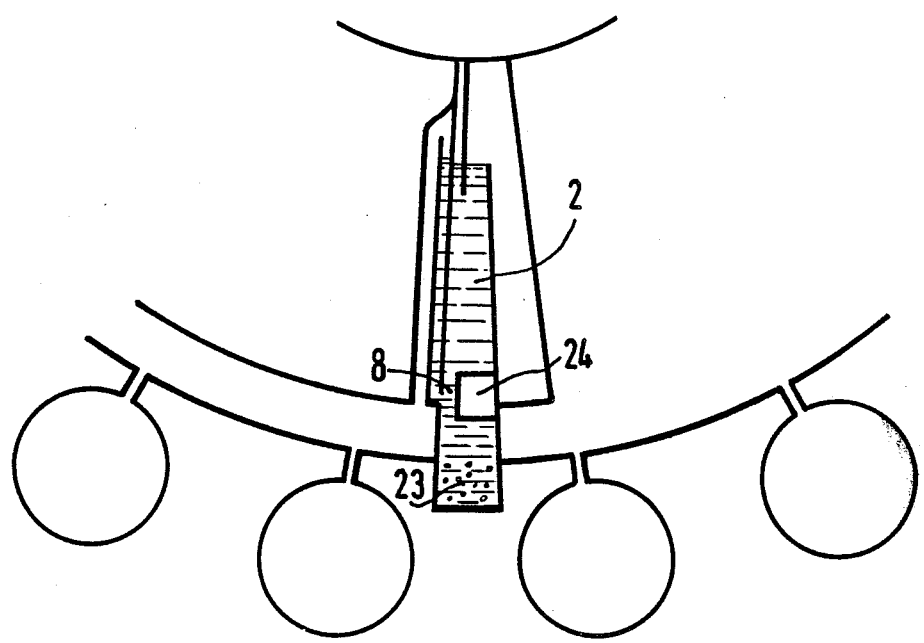

The characteristics and advantages of the invention will be better understood from the following description given only as an example, with reference to the attached schematic diagrams in which:

FIG. 1 is a partial view from the top of a rotor of the invention comprising two calibration vessels and a single mixing vessel, FIG. 2 is a partial view of a rotor comprising several sectors, FIG. 3 is a partial view of a rotor in which a calibration vessel is provided with a siphon, FIG. 4 is a partial view of a rotor in which a calibration vessel comprises an additional volume for decantation.

In FIG. 1, the rotor comprises a central receptacle 1 connected through an orifice 6 to a calibration vessel 2. The vessel 2 is itself connected through an orifice 7 to an overflow vessel 3. The calibration vessel 2 connects via an orifice 8 with the mixing vessel 4, either directly, or via a capillary 9. The mixing chamber 4 is itself connected to the various measuring cells 5 via tubes 10. The rotor comprises another central receptacle 11 for the dilution liquid connected via an orifice 12 to another calibration vessel 13, the latter being connected via orifice 14 to the overflow vessel 3 or to another analogous vessel which is not represented.

It is understood that the dimensions of the central receptacles, the vessels and the measuring cells can vary widely and are determined as a function of the requirements of the analysis.

In FIG. 2, the rotor is subdivided into these sectors each comprising at least two central receptacles 15 and 16, two calibration vessels 17, 18 an overflow vessel 19 and a mixing vessel 20.

In FIG. 3, orifice 8 of vessel 2 extends in the form of a siphon 21 whose elbow 22 is slightly above the level of the overflow orifice 7. During rotation of the rotor, the capillary forces are negligible compared to the centrifugal forces and the liquid air interface take the shape of a cylinder of revolution whose axis is common with that of the rotor and the radius is equal to the distance from the center of the rotor to the orifice 7. When the rotor stops, the capillary forces again become signficant and a small mass of liquid enters the siphon, and this is sufficient to attract and empty the remaining liquid upon subsequent start of the motor.

In FIG. 4, the calibration vessel 2 is extended by an additional volume 23 into which can be collected a precipitate separated by the centrifuging action. It desired, it is possible to increase the precision of the calibration by placing a block 24 opposite the exit orifice 8 which reduces the flow area of the cell 2 towards the volume 23.

Of course, the respective dimensions of the central receptacles, the vessels and the cells can very widely and are determined as a function of the requirements of the analysis.

I claim:

1. A rotor of a centrifuge analysis device, the rotor having a center and a periphery which rotor comprises from the center of the periphery thereof:
   (1) central receptacles for liquids to be diluted before analysis,
   (2) calibration vessels and overflow vessels disposed circumferentially adjacent to each other in respect to a circle concentric with the rotor, the calibration and overflow vessels thereby being spaced at substantially the same distance from the center of the rotor, and wherein each calibration vessel is provided with
      (i) a feed orifice through which it communicates with one of the central receptacles,
      (ii) an exit orifice located in the wall of said calibration vessel opposite the feed orifice and permanently open, and
      (iii) an overflow orifice located at a position between said feed and exit orifices and through which the calibration vessel is connected to one of the overflow vessels, the exit orifice of said calibration vessel having a cross sectional area much smaller as compared to that of the feed and overflow orifices that during the time taken to fill the calibration vessel practically no fluid escapes from said exit orifice,
   (3) a mixing vessel communicating with each calibration vessel through the exit orifice of said calibration vessel, and
   (4) a plurality of measuring cells, each connected to the mixing vessel through a duct.

2. A rotor according to claim 1 wherein the exit orifice of at least one of the calibration vessels has a capillary cross sectional area.

3. A rotor according to claim 1 wherein the exit orifice from at least one of the calibration vessel is a capillary passage oriented tangentially with respect to the wall of said calibration vessel which is opposite to the feed orifice of said vessel.

4. A rotor according to claim 1 wherein the mixing vessel is subdivided into several sectors, each of which is connected to at least two calibration vessels.

5. A rotor according to claim 1 wherein the exit orifices of two adjacent calibration vessels are also adjacent and connected through a common capillary passage with the mixing vessel.

6. A rotor to claim 1 wherein the exit orifice of at least one calibration vessel connects with a siphon having an elbow which is at substantially the same distance from the center of the rotor as the overflow orifice of said calibration vessel, said siphon communicating with the mixing vessel.

7. A rotor according to claim 1 wherein the exit orifice of at least one calibration vessel connects with a siphon having an elbow which is at a distance from the center of the rotor which is a few millimeters greater than the distance of the overflow orifice of said calibration vessel from the center of the rotor, said siphon communicating with the mixing vessel.

8. A rotor according to claim 1 wherein at least one calibration vessel comprises means defining an additional volume for collecting a centrifuged precipitate, said volume extending from the level of the exit orifice of said calibration vessel towards the periphery of the rotor.

* * * * *